United States Patent [19]
Silver

[11] Patent Number: 5,965,149
[45] Date of Patent: Oct. 12, 1999

[54] GRANULAR FORMULATION OF BIOLOGICAL ENTITIES WITH IMPROVED STORAGE STABILITY

[75] Inventor: Scott C. Silver, Bend, Oreg.

[73] Assignee: Thermo Trilogy Corporation, Columbia, Md.

[21] Appl. No.: 08/284,072

[22] Filed: Feb. 14, 1994

Related U.S. Application Data

[63] Continuation-in-part of application No. 08/106,200, Aug. 13, 1993, abandoned.

[51] Int. Cl.$^6$ .............................. A01N 25/28; A01N 25/00
[52] U.S. Cl. ...................... 424/405; 424/93.1; 424/408; 435/1.1; 800/8; 119/6.7
[58] Field of Search .................................. 424/93.1, 405, 424/408; 435/1.1; 800/2, DIG. 5; 119/6.7; 427/2.13, 2.14, 2.15

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,417,545 | 11/1983 | Finney | 119/6.6 |
| 4,568,559 | 2/1986 | Nuwayser et al. | 427/2.15 |
| 4,615,883 | 10/1986 | Nelsen et al. | 119/6.7 |
| 4,647,536 | 3/1987 | Mosbach et al. | 435/177 |
| 4,663,286 | 5/1987 | Tsang et al. | 435/178 |
| 4,701,326 | 10/1987 | Nelsen et al. | 424/408 |
| 4,765,275 | 8/1988 | Yukawa et al. | 119/15 |
| 4,778,749 | 10/1988 | Vasington et al. | 435/2 |
| 4,798,786 | 1/1989 | Tice et al. | 435/177 |
| 4,803,168 | 2/1989 | Jarvis, Jr. | 435/240.22 |
| 4,806,355 | 2/1989 | Goosen et al. | 424/424 |
| 4,814,274 | 3/1989 | Shioya et al. | 435/174 |
| 4,859,377 | 8/1989 | Shasha | 264/4.1 |
| 5,042,427 | 8/1991 | Bedding | 119/6.7 |
| 5,093,130 | 3/1992 | Fujii et al. | 424/463 |
| 5,170,144 | 12/1992 | Nielsen | 335/229 |
| 5,183,950 | 2/1993 | Popiel et al. | 800/2 |
| 5,358,863 | 10/1994 | Quimby et al. | 435/178 |

FOREIGN PATENT DOCUMENTS

| | | |
|---|---|---|
| 256873 | 2/1988 | European Pat. Off. . |
| 93/00816 | 1/1993 | WIPO . |

OTHER PUBLICATIONS

Capinera et al.,, J. Agric. Entomol. (1987) 4:337.
Connick et al., Biological Control 1:281–287 (1991).

*Primary Examiner*—Bruce R. Campell
*Assistant Examiner*—Anne-Marie Baker
*Attorney, Agent, or Firm*—Quarles & Brady LLP

[57] ABSTRACT

A method for preparing granules containing pesticidal or herbicidal biological organisms which can be stored for prolonged periods and conveniently dispensed is provided. Compositions are provided which comprise granules containing entomopathogenic nematodes. Methods for controlling insects, comprising applying the composition to a plant or field is also disclosed.

10 Claims, 3 Drawing Sheets

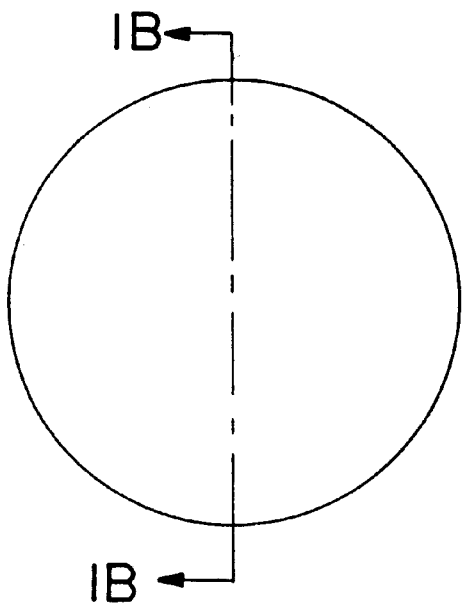
FIG.IA
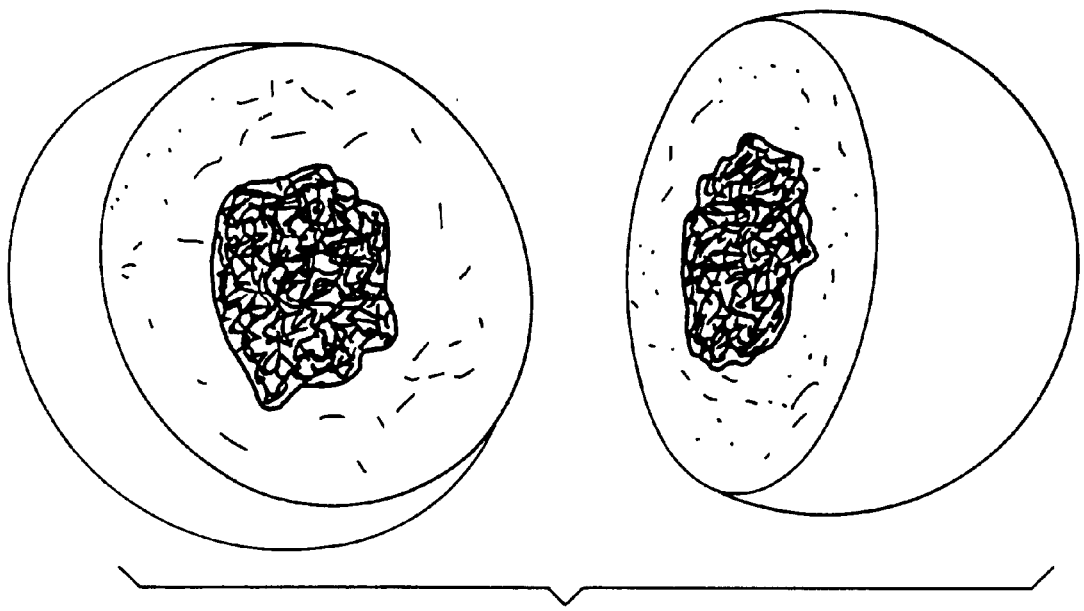
FIG.IB

GRANULAR FORMULATION OF BIOLOGICAL ENTITIES WITH IMPROVED STORAGE STABILITY

This application is a continuation in part of U.S. application Ser. No. 08/106,200 filed Aug. 13, 1993, now abandoned.

BACKGROUND OF THE INVENTION

1. Field of the Invention

The invention relates to methods and compositions for storing and distributing pesticidal or herbicidal biological organisms, in particular entomopathogenic nematodes, for use as agricultural pest control agents. More specifically, the invention concerns new methods for producing granules and for formulating nematodes into such granules for prolonged storage and convenient application.

2. Background Art

The desirability of using entomopathogenic nematodes in compositions to control pests in agricultural contexts has been clearly recognized (Gaugler et al., *ENTOMOPATHOGENIC NEMATODE IN BIOLOGICAL CONTROL*, CRC Press, 1990). The general classification "nematodes" includes roundworms of astounding variety ranging in size from ultramicroscopic to worms of several feet in length. In many cases, these organisms are parasitic, and their mechanisms of parasitism and their targets are as varied as their size range. While many species of nematode are themselves plant pathogens and an agricultural nuisance, a relatively benevolent group of nematodes which infect insect pests have a useful function. In particular, control of insect infestation of plants has been attempted using the "infective juvenile" (IJ) stage of these entomopathogenic nematodes. In this form, the infective juvenile enters the host insect through the alimentary canal or spiracles, emerges from its protective sheath, and penetrates into the host insect's hemocoel. There, the nematode releases symbiotic bacteria which induce septicemia that kills the host, rendering the host corpse suitable for nematode foraging and reproduction. Several generations may be spent within the insect host until food consumption and overpopulation trigger production of another IJ stage generation. The new IJs must then find fresh hosts.

In the IJ stage, the nematodes do not eat, but depend upon internal food stores; however, they do require oxygen, and, unless induced into a cryptobiotic desiccated state, require the presence of water. A major problem associated with the use of IJ nematodes as pesticides resides in the necessity to maintain the IJs in a viable state for extended time periods. The IJs cannot be kept viable simply by harvesting them from, for example, an artificial culture, and placing them in a container. The majority of the IJs so prepared will die within hours. Attempts to overcome this problem have included inducing a "cryptobiotic" state by dehydration or other means which reduce the metabolism to the point where the IJ essentially becomes inert. It is known that nematodes in the soil may exist in such a cryptobiotic state under dry climatic conditions; however, the statistics of this process are not favorable to preserving large numbers of IJs. Alternative drying means which result in a cryptobiotic state with some degree of efficiency are described, for example, in European Patent Publication No. 256,873.

In an alternative approach, the IJs are stored on various moist, high surface area materials. For example, Finney, U.S. Pat. No. 4,417,545, describes a method and package for storage and shipment of nematodes which comprises essentially a water-retaining foam sandwich. While the container is stated to be "suitable for storing nematodes", only nematode eggs were tested. Notably, only one particular foam was found to be successful in maintaining the viability of the eggs, even when storage was at temperatures as low as −5° C.

Yukawa, U.S. Pat. No. 4,765,275 describes a packaging system for nematode storage and transport, wherein nematodes are homogeneously mixed with materials described as adsorbents (e.g., activated charcoal) and stored as a suspension under conditions which prevent microbial growth.

Nelsen et al., U.S. Pat. No. 4,615,883, describes a formulation in which the IJs are encapsulated in an alginate gel obtained by adding calcium ions to a sodium alginate suspension of the nematodes. In these preparations, capsules of 0.5–5 mm in diameter are formed and are said to improve the storageability of the IJs. The use of alginate gels and other encapsulating materials to encapsulate living tissue or cells (though not specifically IJs) has an extensive literature. See, for example, U.S. Pat. Nos. 4,409,331; 4,407,957; 4,391,909; 4,352,883; 4,663,286; 4,778,749; 4,798,786; 4,803,168; 4,806,355; 4,647,536; and 4,814,274. All of these documents describe methods to encapsulate living cells or tissues in various polymeric capsules. The purpose of the capsules in each case is to preserve the viability of the living tissue and, also, to facilitate the use of such tissue in its intended application.

U.S. patent application Ser. No. 07/313,594, filed Feb. 21, 1989, abandoned, assigned to the same assignee and incorporated herein by reference, describes a packaging method for IJs in a reversibly cross-linked matrix which is embedded in a supporting screen. The screen containing the sheet matrix is simply placed in the location of end use, and application of water and an active decross-linking agent liberates the embedded nematodes from the film.

U.S. Pat. No. 5,170,744 (Dec. 15, 1992), commonly assigned with the present application, discloses a more convenient and effective manner of preserving viability of IJ nematodes by immobilizing them in a pseudoplastic gel which can be dispensed in the field by applying a suitable shear force. While embedded in the matrix, the nematodes are immobilized, resulting in reduced metabolism and improved viability. However, upon liquefaction of the supporting medium, the nematodes can be readily dispensed in the desired location.

Bedding, U.S. Pat. No. 5,042,427 discloses a range of product types obtained by mixing IJs with an absorbent material (clay) to remove excess surface moisture and to produce partial desiccation. Homogeneous blends as well as non-homogeneous blends of nematodes and absorbents are described, such as a sandwich consisting of a layer of nematodes between two layers of clay. Granules are not disclosed. These products lack the convenience of either water dispersible or directly applied granules. The clay layers are said to be about two centimeters thick, which would appear to serve as a powerful barrier to oxygen diffusion, thus raising questions about adequate oxygenation of the nematodes using this formulation.

Other work discloses methods of producing starch granules containing various biocontrol agents, such as bacteria; nematodes were not specified (U.S. Pat. No. 4,859,377).

Capinera et al., *J. Agric. Entomol.* (1987) 4:337) described a pellet nematode formulation which pellets contained alfalfa meal, wheat flour and other components.

Connick et al. (1991) *Biological Control* 1:281–287, disclosed entrapment of mycoherbicidal fungi in a pasta-like wheat flour dough. The dough, used for weed control, was air-dried and ground into granules which were sized by sieving.

Connick et al., U.S. patent application Ser. No. 07/560,792 (filed Jul. 9, 1990, licensed to the U.S. Agricultural Research Service), describes an extruded or formed granular product in which nematodes are uniformly distributed throughout a wheat gluten matrix. The formulation also included a filler and humectant to enhance nematode survival. Granules are then dried to low moisture to prevent nematode migration and to reduce risk of microbial contamination. Dried granules are very difficult to dissolve; only partial dissolution was achieved, even after submerging of granules in water for 48 hours. Reported nematode survival rates were relatively low. Further, it appears that this product is limited to direct soil application and cannot be used in spray applications.

In many of the above disclosed formulations, the nematodes or other organisms are homogeneously distributed throughout the composition. This is a source of problems, as discussed below, which the present invention has overcome.

A serious problem in the art not yet successfully overcome is that of nematode migration from the formulated preparations currently on the market. For example, nematodes migrate freely from Connick's 'pasta' granules (Connick et al., supra) unless they are dried sufficiently to inactivate the nematodes. Nematodes that migrate to a surface do not typically survive for long. Once at the surface, nematodes will often assume an adaptive behavior known as "nictation", which is the standing upon one end and actively waving their bodies in the air. Nictation dramatically increases metabolic rate, as measured by oxygen consumption, thereby decreasing the length of time that the initial fixed amount of energy reserves will last before depletion. Furthermore, drying of nematodes becomes a significant problem once they are directly exposed to air. With many of the commercially valuable nematodes such as *Steinernema carpocapsae,* air drying leads to death. Further still, nematodes will migrate from the surface of the product and onto, and potentially out of, the packaging in which they were originally contained. Nematodes that leave the safety of their formulated product rapidly succumb to fatal dehydration. The present invention is directed in part to such problems in the art.

Disclosure of the Invention

The invention provides compositions and methods for their production, which compositions are granules encasing biological organisms useful as herbicides or pesticides, in particular beneficial infective juvenile nematodes. The composition and packaging means therefor are useful for storage, shipping, and dispensing. The methods and formulations provided offer convenience and effectiveness and are suitable for large-scale production, long term storage, and distribution of nematode preparations.

The present invention is directed to a storage composition of pesticidal or herbicidal viable biological organisms comprising a granule formed from a powder or mixture of powders having encased therein a soft core containing a quantity of viable biological organisms.

The organisms are preferably maintained in a partially desiccated state, thereby reducing metabolic activity and extending survival in storage. The degree of desiccation can be controlled by appropriate selection of the dry powder composition and the processing mathods.

In the above composition, the powder is preferably selected from the group consisting of a silica, a diatomaceous earth, hydroxyethyl cellulose, a clay, a pregelled clay, a lignosulfonate, a modified starch, a pregelatinized starch, a superabsorbent and a combination of one or more thereof.

The above composition may further contain one or more of an antibacterial agent, an antifungal agent, a humectant, a stabilizing agent, a viscosifier, a wetting agent or other surfactant, and an ultraviolet light-absorbing agent, all of which agents are not toxic to the biological organisms.

In a preferred embodiment, the biological organisms of the composition are beneficial nematodes, most preferably entomopathogenic nematodes. Preferably the nematodes are infective juvenile nematodes. Preferred entomopathogenic nematodes are of the family Steinernematidae or Heterorhabditidae. In another embodiment, the nematode is a molluskicidal nematode of the family Phasmarhabditidae.

Where the organisms are nematodes, the suspension contains nematodes at a concentration of preferably about $10^5$ to about $2 \times 10^6$ per gram of suspension, more preferably about $8 \times 10^5$ to $10^6$ per gram.

The present invention is also directed to a method for preparing a storage composition of pesticidal or herbicidal viable biological organisms, comprising contacting individual drops or droplets of an aqueous suspension containing the organisms with a powder such that the powder completely surrounds each of the drops, wherein moisture within the drops is drawn into the powder causing the powder to form a solidified casing surrounding the drops containing the organism.

The organisms are preferably beneficial nematodes, more preferably infective juvenile entomopathogenic nematodes, preferably of the family Steinernematidae or Heterorhabditidae.

In the above method, the suspension preferably contains nematodes at a concentration of about $10^5$ to about $2 \times 10^6$ per gram of suspension, more preferably at a concentration of about $8 \times 10^5$ to $10^6$ per gram.

In the above methods, the contacting may be performed by manually applying the drops to the powder. The powder is preferably in motion, either rotational or vibrational at the time of the contacting. In another embodiment, the contacting is performed by spraying droplets of the suspension into a falling curtain of powder. The curtain may fall onto a rotating or vibrating surface on which surface consolidation of granules takes place. In another embodiment, the contacting is performed by applying droplets to a powder suspended in an air-suspended fluidized bed or counter-current fluidized bed apparatus.

In the above methods, the powder is preferably selected from the group consisting of a silica, a clay, a pregelled clay, a diatomaceous earth, a hydroxyethyl cellulose, a lignosulfonate, a modified starch, a pregelatinized starch, a superabsorbent and a combination of one or more thereof.

The present invention is further directed to a method of controlling pests, preferably insects, comprising applying a composition as described above to a plant or field to control the pests. The applying may be performed prior to signs of pest infestation to prevent the infestation or after such infestation. In this method, the nematodes are preferably of the family Steinernematidae, Heterorhabditidae or Phasmarhabditidae.

In the method of controlling pests, the composition may be applied as granules to soil or dissolved in water and applied as a liquid, preferably as a spray to soil or to plants.

BRIEF DESCRIPTION OF THE DRAWINGS

FIGS. 1*a* and 1*b* provide schematic drawings of a granule containing a "soft-centered" nematode core.

MODES OF CARRYING OUT THE INVENTION

Figure 2:
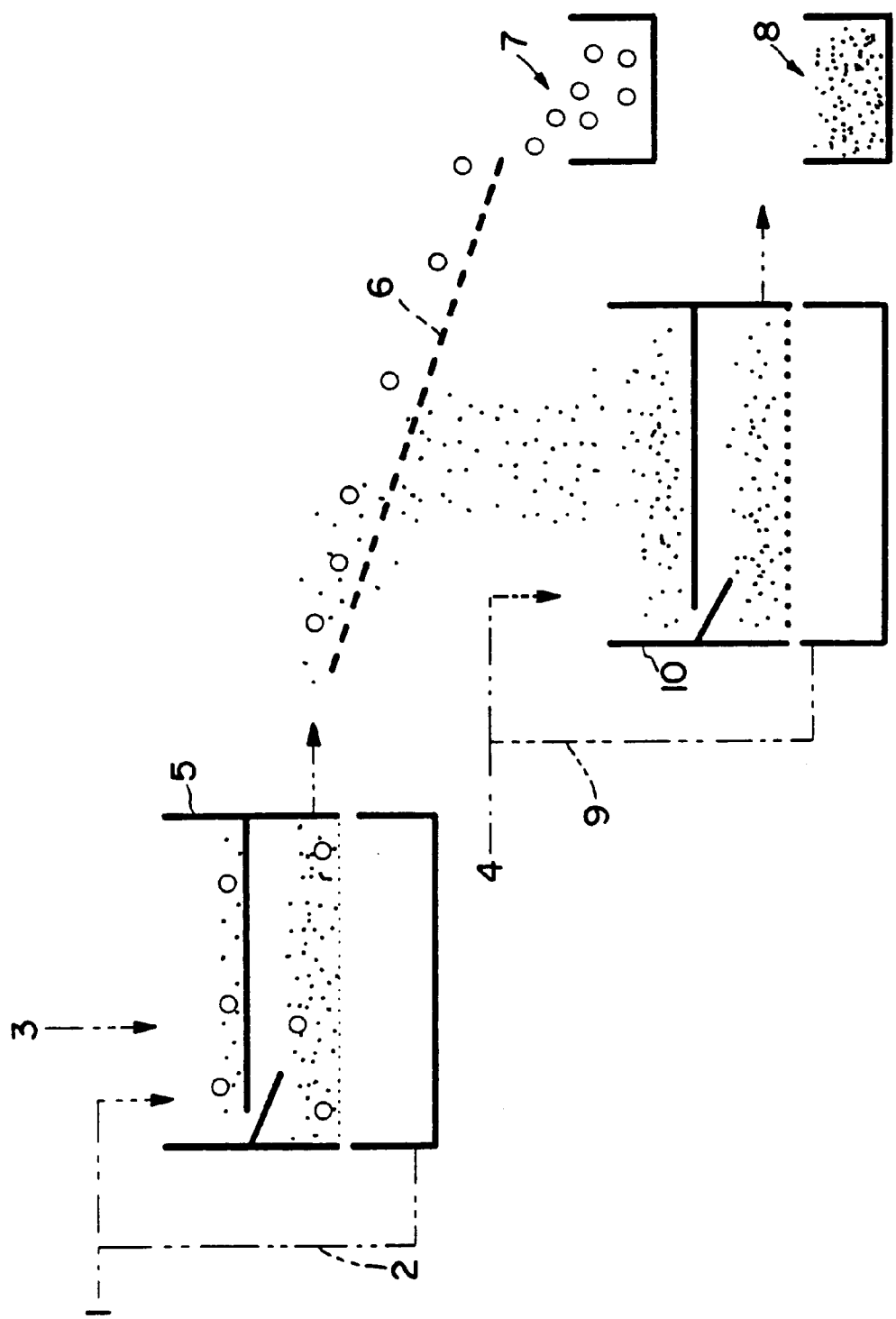
FIG. 2 is a schematic drawing of a process for producing soft-centered granules containing nematodes.

The invention method of forming granules comprises contacting single drops or droplets of an aqueous medium containing pesticidal or herbicidal biological organisms with a powder such that the powder completely surrounds the drop, and moisture from the drop is drawn into the powder to form a solidified casing of powder around the organisms contained within the drop. This results in granules each of which contains a "soft center" of the aqueous medium with the organisms encased within the granule. By the term "granule" is intended a small grain or pellet. By the term "soft centered" granule is intended a granule in which the added organisms initially present in the aqueous suspension around which the granule forms is not homogeneously distributed within the granule such that a substantially larger number of organisms are localized within the central region of the granule than would be expected by chance alone. The biological organisms suspended in the aqueous suspension are thus "encased" by the powder, indicating that they are concentrated in a soft center completely surrounded by the powder material which has drawn water from the originally introduced drop. Control of the amount of water removed from the drop results in the encased organisms being present in a partially desiccated state.

This method is particularly useful for formulating granules containing pesticidal or herbicidal biological organisms for prolonged storage and convenient field application. By the term "pesticidal" is intended a biological organism capable of damaging or killing any type of pest known in the art, ranging from mollusks to insects to mammals. The term "herbicidal" is intended a biological organism capable of inactivating or killing any undesired plant growth. The methods and compositions have broad applicability, for example in the formulation of granules containing herbicidal fungi or bacteria for use in weed control, entomopathogenic nematodes for killing insect pests, molluskicidal nematodes for killing slugs or snail pests, and the like. The granules may also contain organisms which are pathogenic to mammals, such as mice, following ingestion.

A granule according to the present invention is schematically illustrated in FIGS. 1*a* and 1*b*. The novel product formed by this method is useful as an easily dispersible insect pesticide in agriculture or horticulture.

In a preferred embodiment, the method of the present invention has been used to formulate beneficial nematodes in a granule when the aqueous material comprises a suspension of nematode infective juveniles (IJs). By beneficial nematodes are intended any species of nematode which infects pests and has a useful function in agriculture or horticulture, for example, by control of pest infestation of plants. Preferred types of beneficial nematodes are entomopathogenic nematodes.

As set forth in the Background section hereinabove, only certain members of the "nematode" classification are capable of parasitizing and killing insects. The most commonly used species for this purpose is *Steinernema carpocapsae,* also known as *Neoplectana carpocapsae.* Also particularly useful are *S. riobraxis, S. feltiae* (*N. bibionis*), *N. glaseri, S. scapterisci, Heterorhabditis heliothidis* and *H. bacteriophae.* Additional species include: *N. menozzi* (*S. kraussei*), *N. kirjanovae* (*S. glaseri*), *N. georgica* (*S. bibionis*), *N. dutkyi, H. bacteriophora, H. boptha, H. haibletoni, Filipjevimermis leipsandra, Reesimermis nielseni* (*Romanomermis culicivorax*), *Diximermis petersoni, Hexamermis arvalis, Mermis nigrescens,* and *Pheromermis pachysoma.* The foregoing list is not exhaustive, and the method and composition of the present invention is applicable to entomopathogenic nematodes in general.

The present invention is also useful in the killing of non-insect pests which are susceptible to nematode infection. Thus, molluskicidal nematodes which kill snails or slugs may be prepared according to the present invention. Such nematodes are preferably members of the family Phasmarhabditidae, for example, *Phasmarhabditidis hermaphrodita.*

The term "Infective juvenile" or "IJ" refers to an entomopathogenic nematode usually in the third larval stage characterized by retention of the second stage cuticle or sheath after molting to the third stage. In this stage of their development, IJs are capable of vertical and horizontal migration, but depend on internal food stores and do not eat. Nematodes are infectious at this stage of their life cycle.

Methods for culturing entomopathogenic nematodes to obtain larvae in the IJ state are known. In general, it was long thought necessary to provide a substrate-supported medium containing the symbiotic bacteria which are necessary for the IJs to exhibit their entomopathogenic effect. However, more recently it has been found possible to culture such IJs in liquid medium. See, for example, U.S. Pat. No. 5,023,183. The nematodes are grown by any convenient method to the IJ stage, harvested using standard procedures and suspended in water or buffer. Preferred concentrations of IJs for use in the present invention are between about $10^5$ and $2\times10^6$ nematodes per gram of aqueous suspension. More preferably, the nematodes are at a concentration of about $8\times10^5$–$10^6$ IJs per gram of aqueous suspension.

Production of the Granules

The suspension of harvested nematodes is then contacted with a powder under conditions which result in the formation of granules within which a small quantity of aqueous medium containing the nematode IJs is entrapped or encased.

The powder may be one, or a combination of, several different materials, including, silica, ligno-sulfonate, diatomaceous earth, clay, pregelled clay, etc. Table I, below lists a number of particular types of materials used alone or in combination to produce granules according to the present invention. Also listed within each type is one or more particular example, designated by trade name. A person of ordinary skill in the art will readily understand that any of a large number of additional types of powder materials can be used in accordance with the present invention, provided that they are not toxic to the biological organism, for example, the nematodes, which they encapsulate.

TABLE I

| Type of Material | Manufacturer | Name |
|---|---|---|
| Diatomaceous Earth | Eagle Picher | CELATOM FW 60 |
| | Celite | CELITE 209 |
| Hydroxyethyl Cellulose | Union Carbide | CELLOSIZE-QP-4400-H |
| Amorphous Silica | PPG Indust. | HiSil 15 ® |
| Fumed Hydrophobic Silicia | Degussa | AEROSIL R974 |
| Lignosulfonate | Lignotech | D-450-1 |
| | | LIGNOSOL SFX-65 |
| | | MARACARB N-1 |
| | | MARASPERSE N-22 |

TABLE I-continued

| Type of Material | Manufacturer | Name |
| --- | --- | --- |
| | | NORLIG 11DA |
| | | WAFEX |
| Modified Starch | Staley | MIRA-CAP |
| Pregelatinized Starch | National | ULTRA-SPERSE M |
| Attapulgite Clay | P. T. Hutchins | MIN-U-GEL FG< |
| Superabsorbent | Hoechst-Celanese | SAMWET COS915 |
| Pregelled Clay | | ATTAGEL 50--. |

Characteristics of the finished granular product which can be modified by choice of powders include, dissolution rate, mechanical strength, visual appearance (color, texture) retained moisture, initial water activity, microbial stability and compatibility with nematode survival. Properties which affect the ease of manufacture include rate of water absorbance, bulk density, hydrophobicity, and compatibility with other powders in the formulation. A person of ordinary skill in the art will know which powder or combination of powders to select to achieve the desired characteristics of the granules and to optimize the manufacturing process.

Any of a large number of specific devices well-known in the art may be used to produce conveniently the soft-centered nematode granules of the present invention. In one embodiment, droplets of nematode-containing aqueous suspension may be individually dropped upon a bed of powder or powders in a stationary tray or pan and then gently swirled to ensure that the droplets are completely covered by the dry powders. If this material is screened to separate unused powder from the added droplets, it will be seen that the original droplets are uniformly encased with a layer of powder into which excess moisture has diffused. The nematodes within the original aqueous suspension are seen to be tightly bound within the center of the newly formed granule and are all, more or less, evenly protected within their new environment. By selection of the powders used, or by subsequent control of the moisture content, the nematodes can, if desired, be subjected to partial desiccation.

Granules are also conveniently made in a continuous process using any one of a large selection of conventional or special-purpose pieces of agglomeration equipment, including, but not limited to, rotating pans and drums, augers, ribbon blenders, paddle blenders, and similar equipment commonly used for the production of agglomerated and/or coated products.

In another embodiment, granules are made by spraying a nematode-containing aqueous suspension into a falling stream of powdered material and allowing the encasement to occur 'in-flight'. An apparatus known as the Continental Blender (Continental Product Co., Osseo, Wis.) has been used in this process. In yet another embodiment, the drops can be applied by spraying into a powder which is suspended in air in an air-suspended or counter-current fluidized bed apparatus, well-known in the art.

Strength and appearance of granules produced by any of the above methods can be further modified by an additional step in which the newly formed granules are either rolled, tumbled, vibrated or otherwise manipulated to facilitate compaction and consolidation of the powder particles.

Granules may be further modified through a secondary coating process in which a liquid or powder layer is added to the initial encasing layer. This additional layer may be used to enhance mechanical strength, modify dissolution properties, modify water loss properties, protect against microbial contamination, etc. A preferred material for preparation of a second coating of the granule is AEROSIL R974, available from Degussa, a fumed hydrophobic silica which modifies the granule surface in terms of decreasing adherence between granules and improving their appearance.

The size of the granules is in part determined by the drop size and the nature of the particular powder or combination of powders used. With commercially available spray nozzles, it is most convenient to produce individual droplets of aqueous suspension having average diameters of from about 0.05 to 1.2 millimeters. Droplets of this size will generally yield finished granules having average diameters of about 1 to 10 millimeters. If so desired, larger or smaller granules can be formed by varying the conditions of production.

The number of nematodes per granule (or per unit weight of the finished product) can be controlled by adjusting the concentration of nematodes in the aqueous suspension to be encased. For example, with the nematode species *Steinernema carpocapsae*, a suspension can contain from a few hundred to several million IJs per gram of suspension. Larger or smaller nematode species will have different ranges depending on their relative size, as is evident to one of ordinary skill in the art. Preferably, water dispersible granules are formulated from a suspension containing about $10^6$ IJs per gram. Granules designed for direct application (without prior dissolution in water) are optimally prepared at lower concentrations of nematodes so as to achieve uniform ground coverage at an appropriate final concentration.

Higher viabilities of nematodes in the granules are desirable. Preferably, the viability after the storage period is greater than 50%, more preferably, greater than 70%. Of course, application of a larger number of granules can be used to overcome a lower viability in achieving a fixed level of viable nematode application to a given area of soil or plant material.

The relative proportion of powder to nematodes in individual granules can be influenced by the concentration of nematodes in the original suspension. This is particularly true with highly concentrated suspensions wherein the percentage of total volume occupied by nematodes relative to free water is high. Such a suspension is expected to produce granules each having a large nematode-containing center and a relative thin encasing powder layer. Conversely, granules produced from a more dilute nematode suspension are expected to have relative small nematode-containing centers and a relatively thick layer of encasing powder.

The amount of mechanical energy transferred to the newly forming granules can affect compaction of the powders and can thereby modify the mechanical strength and dissolution properties of the granules. In general, the input of additional energy produces granules of greater hardness, greater density and reduced dispersibility.

The granular compositions of the present invention thus consist of a central core, composed largely of basically pure nematodes, surrounded by, and completely encased by, a layer of moistened powdered materials which have been brought together through the techniques associated with their granule formation so as to form a continuous protective coating around the central core of nematodes. The nematodes within the center may or may not be partially desiccated, the degree of desiccation being subject to control by selection of materials and production methods.

The aqueous suspension of nematodes may additionally contain other soluble or insoluble materials, such as fillers and viscosifiers, which contribute to the physical properties of the granules. Thus, one or more powders, for example a lignosulfonate, may be suspended in the aqueous suspension prior to contacting droplets with the bulk powder. One or more wetting agents or other surfactants may be present to modify the droplet size or the way in which the droplets are sprayed. Examples of known surfactants include Morwet EFW and Morwet 3008 (Witco). Viscosifiers such as Nalcotrol® (Nalco Corporation), polyacrylic acids, biological gums such as xanthan may be used. Polymers such as polyvinyl pyrollidone copolymers or block polymers may be included in the aqueous suspension, for example, to increase drop size and decrease drift during spraying. Drop size may also be modulated by the nature of the drop-forming mechanical device, for example, by the nozzle size of the sprayer.

The encasing layer physically restrains the nematodes and prevents migration. The encasing layer also buffers against changes in the product's moisture level by serving both as a dynamic reservoir or sink for excess moisture. The encasing layer further provides physical protection against mechanical disruption. Because the layer completely encases all of the nematodes, they are substantially all equally protected.

By appropriate selection of the formulation materials, granules may be designed to readily disperse (dissolve) in water or to be more suitable for direct soil application with conventional agricultural spreader equipment.

The relatively short distance between the nematodes and the exterior surface of the granule presents little obstacle for oxygen diffusion, and the interstitial spaces between granules provide a convenient path for oxygen diffusion even when the granules are contained within a bulk package.

The methods and compositions of the invention overcome a serious problem in the art, that of nematode migration and death due to subsequent desiccation. The soft centered granules, in which nematodes are highly concentrated in the center, virtually eliminate migration of nematodes from the interior to the surface or beyond. This represents a significant improvement over existing product-types. Because virtually every nematode in the present composition is clustered deep within the center and is prevented from migrating by an encasing barrier, every nematode is equivalently prevented from migrating out of the granule. While inside the granule, the nematode is typically in a state of partial desiccation. This is in contrast with product-types in which nematodes are uniformly and homogeneously dispersed, wherein those nematodes nearer the surface are more apt to migrate and to experience lower moisture conditions than nematodes held more centrally within the composition of the present invention.

It should be noted that the concentration of nematodes within the granule center is one way in which to facilitate a natural and important nematode adaptational behavior known as "aggregation" (Gaugler et al., *ENTOMOPATHOGENIC NEMATODE IN BIOLOGICAL CONTROL*, CRC Press, 1990). Aggregation may be driven by a mechanosensitivity or tactile sensitivity and has survival value in protecting nematodes from desiccation and sunlight. Nematodes at the periphery of aggregations usually die, resulting in formation of a natural barrier against unfavorable environmental stresses, so that survival within the clump is greater than that of isolated individuals on the same substrate. Thus, concentration of nematodes within the center of an encased mass, as described herein, mimics aggregation as it occurs in nature.

Furthermore, as nematodes reproduce within the body of an infected insect larva or maggot, the number within the corpse increases greatly until virtually all that is left is a mass of centrally located nematodes within an encasing shell. Under natural soil conditions, this packet may be partially desiccated as moisture is gradually lost to the environment. As in the granules described herein, this moisture loss can occur very gradually so that the nematodes may adapt themselves for long term survival in a partially desiccated state.

By way of contrast, when *Steinernema carpocapsae* nematodes are homogeneously mixed (rather than entrapped) with dry powders such as those described herein, the non-encased nematodes not only nictate, but also migrate freely. Peak oxygen demands were observed as high as 5.69 ml oxygen/million nematodes/day. Oxygen consumption after 14 days was as great at 1.39 ml oxygen/million nematodes/day, or roughly 3.5 to 7 times as high as measured with nematodes encased according to the present invention. Viability of stored nematodes fell significantly more rapidly in homogeneously mixed formulations then in encased granules and usually dropped below the economically acceptable thresholds within about six weeks or much sooner at 25° C.

The aqueous solution in which the nematodes are suspended, and which is encased in the granule, may further contain one or more additional components which help protect the nematodes from unwanted desiccation or contamination. For example, a bactericidal or fungicidal antibiotic may be added to prevent infection, provided only that this antibiotic is not toxic to the nematodes. In cases where bacterial or fungal contamination of the products may be a problem, the formulation ingredients may be sterilized prior to the addition of nematodes or to the production of the granules, provided that any sterilization procedures do not adversely affect the granule-forming properties of the powder or the efficacy of the final product.

The aqueous suspension may also contain one or more humectants or anti-desiccant materials. Humectant materials may include, but not be limited to glycerol, sugars such as sucrose, invert emulsions and cellulose ethers.

The aqueous solution may also contain one or more stabilizing agents which are inert with respect to the biological activity of the IJs. Such stabilizing agents or fillers may or may not affect the physical properties of the granules. Suitable stabilizing agents are preferably high concentrations of carbohydrate materials, such as 10–20% sucrose or 20–30% dextran. Addition of stabilizing agent enhances the convenience of the formulation. The density should be 1.03–1.1 g/ml.

The granules may contain material, introduced either in the powder or in the aqueous suspension, that protect the nematodes from ultraviolet light when they are applied to soil. Examples of a useful ultraviolet light absorbing materials are lignosulfonates.

Freshly made granules according to the present invention will typically have moisture levels of about 35–55%, more preferably about 40–45%, including the moisture within the nematodes themselves. The "water activity," which is a measure of free reactive water, of freshly made granules typically falls within the range of 0.930 to 0.995 and preferably is in the range of 0.96 to 0.98 for formulations containing the nematode *Steinernema carpocapsae*. Both the properties of moisture level and water activity can be influenced by the absorbency of the dry formulation powder or powders selected, by the water content of the aqueous nematode suspension used, and by the amount of water loss occurring during manufacture.

The methods and compositions of the present invention thus provide nematodes in a granule, which nematodes are encased within the granule's core in a "soft center" comprising a small amount of aqueous material in which they were originally suspended. The "soft center" is surrounded and protected by a coating of a material or materials of varying thickness that contain no or relatively few nematodes. The present inventor has observed that nematodes formulated in this way have a retarded metabolic rate, measured for example by reduced oxygen consumption. Thus, they not only live longer but maintain their pathogenicity longer, allowing prolonged storage of the composition of this invention. When released into the environment, the nematodes potentially have greater energy storage reserves available than nematodes stored more conventionally.

Because of the nature and size of the granules of the present invention, it is also relatively simple to provide for the oxygen requirements of nematodes in this formulation compared to other formulations. The nematodes' oxygen consumption is highest in the first few days after granules are made, and this rate may peak at level of about 3.0 ml oxygen/million nematodes/day with *Steinernema carpocapsae*. The rate of oxygen consumption quickly falls and within about one week, the rate falls to about 0.2–0.4 ml oxygen/million nematodes/day. The lower the rate of oxygen consumption, the longer the nematodes will be able to survive on their initially fixed quantity of metabolic energy sources (mainly lipids). The rates of oxygen consumption in the granular formulations of the present invention are at least as low or lower than the rate in most stable existing products examined. On this basis, nematodes in granular formulations according to the present invention can be expected to survive for at least 6 months at 25° C.

Unexpectedly, the granular formulations according to the present invention have exceptionally good thermostability compared to other product types. Some sample were found to be stable at 30° C. for beyond 7 weeks.

According to the present invention, a combination of two or more compatible species of entomopathogenic nematodes can be combined in a single granule. Furthermore, one or more species of nematodes may be combined with compatible biological or chemical pesticides or herbicides to broaden the advantageous properties of the products of this invention.

Packaging of the Granules

The compositions of the present invention may be packaged in any way compatible with prolonged survival and maintenance of viability of the nematodes. Thus for example, the granules are placed into bottles, preferably made of polypropylene, having volumes in the range of about 50 ml to about four liters. The lid of the bottle is designed to allow adequate oxygenation of the encased nematodes. Thus, the lid preferably has a porous plastic cap that transmits gases between the environment and the bottle.

Because of the desire to maintain a certain level of water activity and prevent water loss, the packaging may include a means to maintain moisture in the desired range, such as a moisture reservoir, an absorbent material containing water, etc.

The number of granules per bottle is preferably such that each bottle contains between about 10 million and 250 million nematodes.

The bottle may be specially adapted for application of the granules to the soil or to other containers containing water for ultimate liquid application of the nematodes to soil or plants. Thus, for example, the top of the bottle may be replaceable by a specially adapted top for direct application of the bottle's contents.

Application of Granules Containing Nematodes

Granules of the present invention may be applied to an agricultural or horticultural environment to kill insect pests. A "pesticidally effective" amount of granules is defined as the amount of granules containing sufficient nematodes to result in a significant level of insect control in an area relative to an untreated area. The actual amount may vary with the particular nematode species contained in the granules, as well as soil conditions and other environmental conditions.

Two preferred modes of applying the granules in the agricultural setting include broadcasting the granules in their granular form or dispersing the granules into water and spraying or otherwise applying the water to the crop or soil. The granules of the present invention not only have the advantage of ease of transportation, but they are particularly easy to use either in intact granular form or as a spray.

Having now generally described the invention, the same will be more readily understood through reference to the following examples which are provided by way of illustration, and are not intended to be limiting of the present invention, unless specified.

EXAMPLES

Examples 1–9, below, are presented to exemplify the production of nematode-containing granules using various mixtures of powders and various species of nematodes. Many additional combinations have been utilized with similar results; for the sake of brevity, all such examples are not presented here.

In Examples 1–9, below, granules were produced essentially as follows. The mixture of powders (indicated in each Example) was placed in pan agglomerator having a diameter of about 16 inches to a thickness of several inches. The pan was tilted about 45°–55° from the horizontal and rotated on its axis at a speed of about 20–40 rpm.

The aqueous suspension of nematode IJs at the indicated concentration was applied as a steady drop-by-drop spray from a syringe tip. Once granules had formed, the mixture of granules and ungranulated powder was passed through a screen which retained the granules and allowed the powder to be recycled.

The granules were stored for varying periods of time at 5° C., 25° C. and 30° C. Samples of 1.5 grams of granules and were tested as shown, generally weekly, for viability (expressed as % viability) and water activity (in units). In some samples, oxygen demand was also tested and expressed in units of ml $O_2$/million nematodes/day.

In several samples, pathogenicity of the nematodes was tested by single infection of 96 wax moth larvae with 96 individual nematodes. The pathogenicity test was "passed" if at least 50% of the nematodes infected and killed the larvae within 72 hours.

Examples 1–16 employ *Steinernema carpocapsae*.

EXAMPLE 1

Powder Composition: 50% CELATOM FW 60 (diatomaceous earth, available from Eagle Picher), 33.3% CELLOSIZE-QP 5200-H (hydroxyethyl cellulose, available from Union Carbide), 16.7% MIRA-CAP (modified starch, available from Staley) Nematode concentration in granules: 630,000/gm

| Time (wks) | Viability (%) | Water Activity | O₂ Demand |     |
|---|---|---|---|---|
| 0 | 96.8 | 0.968 | 1d.:1.73 | 4d:0.25 |
| 1 | 94.6 | 0.951 | 0.17 | |
| 2 | 90.8 | 0.921 | 0.15 | |
| 4 | 86 | 0.969 | | |
| 6 | 95.7 | 0.92 | 0.28 | |

EXAMPLE 2
Powder Composition: 50% HiSil 915®(amorphous silica, available from PPG Indust.), 33.3% CELLOSIZE-QP-5200H (hydroxyethyl cellulose, available from Union Carbide), 16.7% MIRA-CAP (modified starch, available from Staley) Nematode concentration in granules: 460,000/gm

| Time (wks) | Viability (%) | Water Activity | O₂ Demand |     |
|---|---|---|---|---|
| 0 | 91.6 | 0.976 | 1d:1.18 | 4d:0.30 |
| 1 | | | 0.27 | |
| 2 | 91.6 | 0.955 | 0.10 | |
| 4 | 89.8 | | 0.23 | |
| 6 | 93.1 | | 0.15 | |
| 8 | 87.6 | | | |
| 10 | 70.0 | 0.952 | Pathogenicity passed | |
| 12 | 89.4 | 0.974 | | |

EXAMPLE 3
Powder Composition: 50% HiSil 915®(amorphous silica, available from PPG Indust.), 33.3% CELLOSIZE-QP5200-H (hydroxyethyl cellulose, available from Union Carbide), 16.7% MARASPERSE N-22 (a lignosulfate, available from Lignotech) Nematode concentration in granules: 490,000/gm

| Time (wks) | Viability (%) | Water Activity | O₂ Demand |     |
|---|---|---|---|---|
| 0 | 91.0 | 0.972 | 1d:1.45 | 4d:0.47 |
| 1 | | | 0.36 | |
| 4 | 91.8 | | 0.30 | |
| 6 | 93.2 | | 0.26 | |
| 8 | 90.5 | | | |
| 10 | 85.0 | 0.964 | Pathogenicity passed | |
| 12 | 88.4 | 0.974 | | |

EXAMPLE 4
Powder Composition: 43% Celation FW60, 28.5% CELLOSIZE-QP-4400-H (hydroxyethyl cellulose, available from Union Carbide), 28.5% Mira-cap Nematode concentration in granules: 540,000/gm

| Time (wks) | Viability (%) | Water Activity | O₂ Demand |     |
|---|---|---|---|---|
| 0 | 98.6 | 0.976 | 1d.:1.01 | 5d:0.350 |
| 1 | 96.4 | | 0.25 | |
| 2 | 94.9 | | 0.31 | |
| 4 | 93.0 | | 0.32 | |
| 6 | 90.4 | | 0.15 | |
| 8 | 88.1 | 0.971 | | |
| 10 | 90.4 | 0.972 | | |

EXAMPLE 5
Powder Composition: 43% CELATOM FW 60 (diatomaceous earth, available from Eagle Picher), 14.2% CELLOSIZE-QP-4400-H hydroxyethyl cellulose, available from Union Carbide), 14.2% CELLOSIZE-QP-5200-H (hydroxyethyl cellulose, available from Union Carbide), 28.6% MIRA-CAP (modified starch, available from Staley) Nematode concentration in granules: 450,000/gm

| Time (wks) | Viability (%) | Water Activity | O₂ Demand |     |
|---|---|---|---|---|
| 0 | 98.6 | 0.976 | 1d.:1.38 | 5d:0.39 |
| 1 | 93.4 | | 0.29 | |
| 2 | | | 0.33 | |
| 4 | 90.3 | | 0.28 | |
| 6 | 86.8 | | | |
| 8 | 86.0 | | | |
| 10 | 84.7 | 0.973 | | |

EXAMPLE 6
Powder Composition: 50% HiSil 915®(amorphous silica, available from PPG Indust.), 33.3% LIGNOSOL SFX-65 (a lignosulfate, available from Lignotech), 16.7% MIRA-CAP (modified starch, available from Staley) Nematode concentration in granules: 460,000/gm

| Time (wks) | Viability (%) | Water Activity | O₂ Demand |     |
|---|---|---|---|---|
| 0 | 99.1 | 0.968 | 1d.:1.0 | 45d:0.31 |
| 1 | 95.6 | | 0.38 | |
| 2 | 93.0 | | | |
| 6 | 90.8 | | | |
| 8 | 91.3 | 0.974 | | |
| 10 | 93.8 | 0.978 | | |

EXAMPLE 7
Powder Composition: 50% HiSil 915®(amorphous silica, available from PPG Indust.), 33.3% LIGNOSOL SFX-65 (a lignosulfate, available from Lignotech), 16.6% MIRA-CAP (modified starch, available from Staley), Nematodes in 5% LIGNOSOL SFX-65) Nematode concentration in granules: 490,000/gm

| Time (wks) | Viability (%) | Water Activity | O₂ Demand |     |
|---|---|---|---|---|
| 0 | 97.6 | 0.968 | 1d.:0.86 | 4d:0.43 |
| 1 | 93.0 | | 0.25 | |
| 2 | 93.1 | | | |
| 6 | 89.0 | | | |
| 8 | 90.0 | 0.970 | | |
| 10 | 92.9 | 0.973 | | |

EXAMPLE 8
Powder Composition: 50% HiSil 915®(amorphous silica, available from PPG Indust.), 33.3% LIGNOSOL SFX-65 (a lignosulfate, available from Lignotech), 16.7% MIRA-CAP (modified starch, available from Staley) Nematode concentration in granules: 550,000/gm

| Time (wks) | Viability (%) | Water Activity | O₂ Demand |     |
|---|---|---|---|---|
| 0 | 97.7 | 0.964 | 1d.:1.1 | 45d:0.21 |
| 1 | | | 0.23 | |
| 2 | 90.0 | | | |

-continued

| Time (wks) | Viability (%) | Water Activity | O₂ Demand |
|---|---|---|---|
| 6 | 86.8 | 0.973 | |
| 8 | 91.2 | 0.972 | |
| 10 | 75.2 | 0.973 | |

EXAMPLE 9
Powder Composition: 37.5% HiSil 915®(amorphous silica, available from PPG Indust.), 36% LIGNOSOL SFX-65 (a lignosulfate, available from Lignotech), 3.1% NORLIG 11DA (a lignosulfate, available from Lignotech), 20.1% MIN-U-GEL FG(attapulgite clay, available from P. T. Hutchins), 3.1% ULTRA-SPERSE M (a pregelatinized starch, available from National), 0.2% Topsin 70WP Nematode concentration in granules: 560,000/gm

| Time (wks) | Viability (%) | Water Activity | O₂ Demand | |
|---|---|---|---|---|
| 0 | 97.9 | 0.972 | 1d.:0.53 | 4d:0.30 |
| 1 | | | 0.30 | |
| 2 | 92.6 | 0.962 | | |
| @ 03° C. | 94.7 | | | |
| 4 | 94.6 | 0.959 | | |

EXAMPLE 10
Powder Composition: 37.5% HiSil 915®(amorphous silica, available from PPG Indust.), 36% LIGNOSOL SFX-65 (a lignosulfate, available from Lignotech), 3.1% NORLIG 11DA (a lignosulfate, available from Lignotech), 20.1% MIN-U-GEL FG(attapulgite clay, available from P. T. Hutchins), 3.1% ULTRA-SPERSE M (a pregelatinized starch, available from National), 0.2% Sorbic Acid Nematode concentration in granules: 580,000/gm

| Time (wks) | Viability (%) | Water Activity | O₂ Demand | |
|---|---|---|---|---|
| 0 | 96.6 | 0.965 | 1d.:0.64 | 45d:0.33 |
| 1 | | | 0.36 | |
| 2 | 94.9 | 0.959 | | |
| @ 30° C. | 93.3 | | | |
| 4 | 93.9 | 0.962 | | |

EXAMPLE 11
Powder Composition: 37.5% HiSil 915®(amorphous silica, available from PPG Indust.), 36% LIGNOSOL SFX-65 (a lignosulfate, available from Lignotech), 3.1% NORLIG 11DA (a lignosulfate, available from Lignotech), 20.1% MIN-U-GEL FG(attapulgite clay, available from P. T. Hutchins), 3.1% ULTRA-SPERSE M (a pregelatinized starch, available from National), 0.2% Methyl Paraben Nematode concentration in granules: 520,000/gm

| Time (wks) | Viability (%) | Water Activity | O₂ Demand | |
|---|---|---|---|---|
| 0 | 91.7 | 0.976 | 1d.:0.82 | 4d:0.32 |
| 1 | | | 0.24 | |
| 2 @ 30° C. | 92.7 | | | |

EXAMPLE 12
Powder Composition: 37.5% HiSil 915®(amorphous silica, available from PPG Indust.), 36% LIGNOSOL SFX-65 (a lignosulfate, available from Lignotech), 3.1% NORLIG 11DA (a lignosulfate, available from Lignotech), 20.1% MinOU-Gel FG, 3.1% Ultrasperse M, 0.2% cupric sulfate Nematode concentration in granules: 490,000/gm

| Time (wks) | Viability (%) | Water Activity | O₂ Demand | |
|---|---|---|---|---|
| 0 | 98.0 | 0.974 | 1d.:0.76 | 4d:0.28 |
| 1 | | | 0.22 | |
| 2@30°C. | 93.0 | | | |
| 4 | 97.3 | 0.969 | | |

EXAMPLE 13
Powder Composition: 49.8% HiSil 915®(amorphous silica, available from PPG Indust.), 16.7% LIGNOSOL SFX-65 (a lignosulfate, available from Lignotech), 16.7% MARA-CARB N1 (a lignosulfate, available from Lignotech), 16.7% MIRA-CAP (modified starch, available from Staley), 0.2% sorbic acid Nematode concentration in granules: 350,000/gm

| Time (wks) | Viability (%) | Water Activity | O₂ Demand | |
|---|---|---|---|---|
| Expt. 1 (Nematode concentration in granules: 350,000/gm) | | | | |
| 0 | 95.4 | 0.955 | 1d:0.69 | 4d:0.32 |
| 1 | | | 0.37 | |
| 2 | 95.5 | 0.952 | | |
| 4 | 89.6 | 0.951 | | |
| Expt. 2 (Nematode concentration in granules: 510,000/gm) | | | | |
| 0 | 97.1 | 0.966 | 1d:0.59 | 4d:0.21 |
| 1 | | | 0.21 | |
| 4 | 95.0 | 0.962 | | |

EXAMPLE 14
Powder Composition: 32.8% HiSil 915®(amorphous silica, available from PPG Indust.), 26% MIN-U-GEL FG(attapulgite clay, available from P. T. Hutchins), 8.5% LIGNOSOL SFX-65 (a lignosulfate, available from Lignotech), 3% NORLIG 11DA (a lignosulfate, available from Lignotech), 3% ULTRA-SPERSE M (a pregelatinized starch, available from National), 13% CELITE 209 (diatomaceous earth, available from Celite), 2.5% Morwet EFW, 2.5% Morwet 3008, 8.5% MARACARB N1 (a lignosulfate, available from Lignotech), 0.2% Sorbic Acid

| Time (wks) | Viability (%) | Water Activity | O₂ Demand | |
|---|---|---|---|---|
| Expt. 1 (Nematode concentration in granules: 510,000/gm) | | | | |
| 0 | 94.0 | 0.965 | 1d:1.10 | 4d:0.27 |
| 1 | | | 0.21 | |
| 2 | 94.0 | 0.963 | | |
| Expt. 2 (Nematode concentration in granules: 410,000/gm) | | | | |
| 0 | 93.2 | 0.967 | 1d:1.01 | 4d:0.44 |
| 1 | | | 0.32 | |
| 2 | 91.9 | 0.968 | | |

EXAMPLE 15
Powder Composition: 32.7% HiSil 915®(amorphous silica, available from PPG Indust.), 12.9% CELITE 209 (diatomaceous earth, available from Celite), 8.5% LIGNOSOL SFX-65 (a lignosulfate, available from Lignotech), 8.5% MARACARB N1 (a lignosulfate, available from Lignotech), 3.0% NORLIG 11DA (a lignosulfate, available from Lignotech), 5.3% Miracap, 3.0% Ultrasperse M, 26.1% MIN-U-GEL FG(attapulgite clay, available from P. T. Hutchins).

| Time | Viability % | |
|---|---|---|
| (wks) | 25c | 30c |
| 0 | 96.0 | 96.0 |
| 1 | | 93.0 |
| 2 | | 96.6 |
| 3 | | 92.7 |
| 4 | 92.8 | 94.6 |
| 5 | | 92.5 |
| 6 | 95.5 | 92.6 |
| 7 | | 92.9 |
| 8 | | 80.4 |
| 9 | 89.6 | 72.4 |
| 10 | 88.2 | |

EXAMPLE 16

Powder Composition: 57.1% HiSil 915®(amorphous silica, available from PPG Indust.), 28.6% LIGNOSOL SFX-65 (a lignosulfate, available from Lignotech), 14.3% Miracap. Nematode concentration in granules: 580,000/gm

| Time | Viability % | | Water Activity |
|---|---|---|---|
| (wks) | 25c | 30c | 25c |
| 0 | 98.4 | 98.4 | 0.983 |
| 1 | | 95.8 | |
| 2 | 98.2 | 95.8 | 0.983 |
| 3 | | 94.4 | |
| 4 | 95.2 | 94.2 | 0.977 |
| 5 | | 94.3 | |
| 6 | 92.9 | 83.9 | 0.975 |
| 7 | | 83.5 | |
| 8 | 94.9 | | 0.971 |
| 11 | 93.2 | | 0.971 |
| 12 | 91.3 | | 0.972 |

EXAMPLE 17

*Steinernema feltiae*
Powder Composition: 39.3% CELITE 209 (diatomaceous earth, available from Celite), 27.7% ATTAGEL 50 (pregelled clay, available from Hoechst-Celanese), 11.0% LIGNOSOL SFX-65 (a lignosulfate, available from Lignotech), 11.0% Miracap, 11.0% Star-Dri 10. Nematode concentration in granules: 318,000/gm

| Time | Viability % | |
|---|---|---|
| (wks) | 25c | 30c |
| 0 | 95.3 | 95.3 |
| 0.6 | | 93.0 |
| 1 | 95.3 | 94.7 |
| 2 | 95.2 | 94.7 |
| 3 | | 93.8 |
| 4 | 95.4 | 90.6 |
| 5 | 92.5 | 91.0 |
| 6 | 91.5 | 83.5 |

EXAMPLE 18

*Steinernema scapterisci*
Powder Composition: 39.3% CELITE 209 (diatomaceous earth, available from Celite), 27.7% ATTAGEL 50 (pregelled clay, available from Hoechst-Celanese), 11.0% LIGNOSOL SFX-65 (a lignosulfate, available from Lignotech), 11.0% Miracap, 11.0% Star-Dri 10.

| Time | Viability % | |
|---|---|---|
| (wks) | 25c | 30c |
| 0 | 95.0 | 95.0 |
| 0.6 | | 96.9 |
| 1 | | 97.0 |
| 2 | | 94.6 |
| 3 | | 95.5 |
| 4 | | |
| 5 | 95.6 | 87.3 |
| 6 | 94.3 | 93.0 |

EXAMPLE 19

*Steinernema riobravis*
Powder Composition: 39.3% CELITE 209 (diatomaceous earth, available from Celite), 27.7% ATTAGEL 50 (pregelled clay, available from Hoechst-Celanese), 11.0% LIGNOSOL SFX-65 (a ligosulfate, available from Lignotech), 11.0% Miracap, 11.0% Star-Dri 10.

| Time | Viability % | |
|---|---|---|
| (wks) | 25c | 30c |
| 0 | 88.9 | 88.9 |
| 0.6 | | 81.0 |
| 1 | | 90.3 |
| 2 | | 85.3 |
| 3 | | 77.7 |
| 4 | | |
| 5 | 84.6 | 85.6 |
| 6 | 90.1 | 75.2 |

EXAMPLE 20

MANUAL PRODUCTION OF NEMATODE GRANULES USING OSCILLATORY GRANULATION

An 8 inch diameter coated cake pan was affixed horizontally to a laboratory vortex mixer. Powdered materials were placed in the pan and the mixer turned on an adjusted to the optimal speed such that the powder danced and swirled in the pan. By placing a hand on the outside of the pan, the powders were made to cycle more vigorously around the pan, and flowed as a broad band across a considerable portion of the pan's surface.

A nematode slurry was added dropwise to the moving powders. Individual droplets quickly rolled up and became uniformly covered in powder, absorbed the excess water and formed discrete granules. Newly formed granules rolled and danced within the pan. A deflector was used to divert recently formed granules from the area were additional slurry was being dropped to avoid creating multiply-sized granules.

EXAMPLE 21

PRODUCTION OF NEMATODE GRANULES USING OSCILLATORY GRANULATION IN A CONTINUOUS PROCESS

Figure 3:
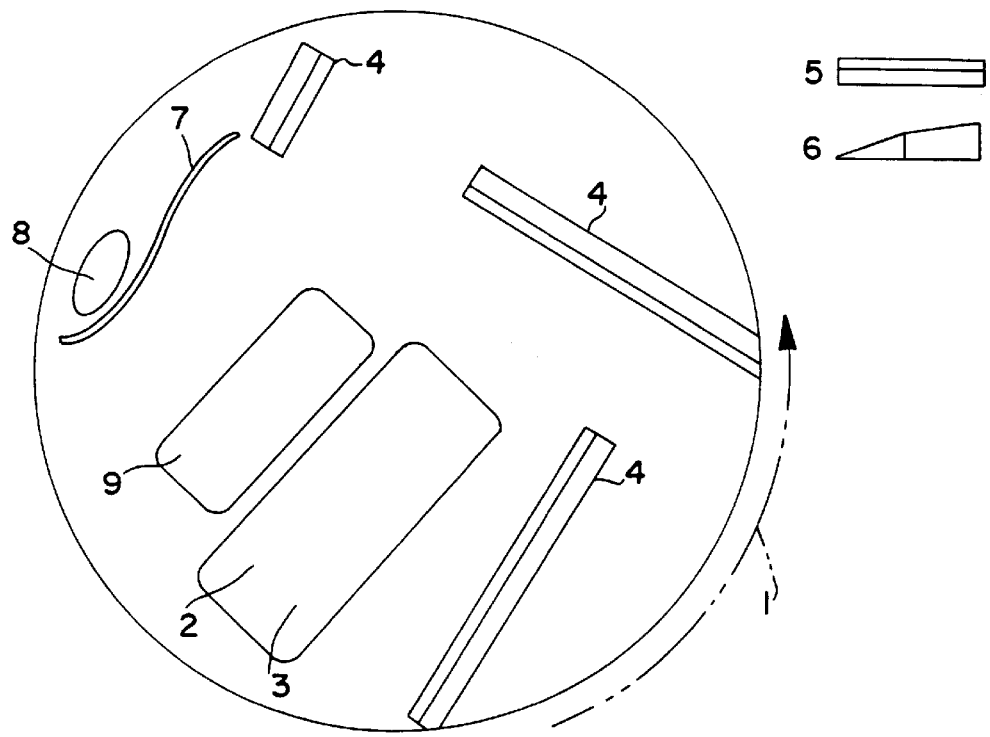
FIG. 3 provides a sample layout of a modified vibrating orbital screener used to make soft-centered granules.

FIGS. 2 and 3 illustrate a process and apparatus for forming and optionally coating granules in a continuous operation. The process employs two vibratory screeners and a vibratory screen conveyor. Only a single pan is required to make uncoated granules. The pan may be pretreated by coating with a non stick material or with a teflon film, either over its entire surface or over the coated spray landed area.

Nematode slurry is dropped as individual drops onto powders moving within the pan. A narrow rectangular pattern of dropping is oriented along a radius. Fresh or recycled powder is continuously dropped upon the powder landing zone (see FIG. 3), directly "upstream" from the "spray drop landing zone." By using appropriately placed flow diverters, separation of the dense granules from the lighter powder is facilitated. The diverters redirect the powder toward the center while granules pass over them, moving toward the perimeter and eventually dropping through the "granule take off hole" (FIG. 3).

An impassable "retaining barrier" (FIG. 3) forms a passage leading to the "granule take off hole" and, on the other side, forms an obstacle to powders and granules which have not yet migrated into the orbit of the passage way. Diverted materials are directed to avoid reentering the "powder landing zone" passing by nearer the outside edge.

Material falling through the granule take off hole lands upon the screen, which is a fine mesh screen or a combination of a coarser screen underlaid by a fine mesh screen. The granules are ultimately subjected to fine screening to remove fines and ungranulated powder. Granules are discharged from this screen while fines are collected in a bottom pan and are recycled to the granulation pan along with fresh powder.

A vibratory screen conveyor is used to separate oversized granules ("overs") from correctly sized granules. If a second coating layer is desired, the granules passing through this screen are dropped onto a second similarly modified pan containing powders for secondary coating.

The final product, comprising correctly sized nematode containing granules, are collected and packaged.

EXAMPLE 22

ROTATION PROCESS

Figure 4:
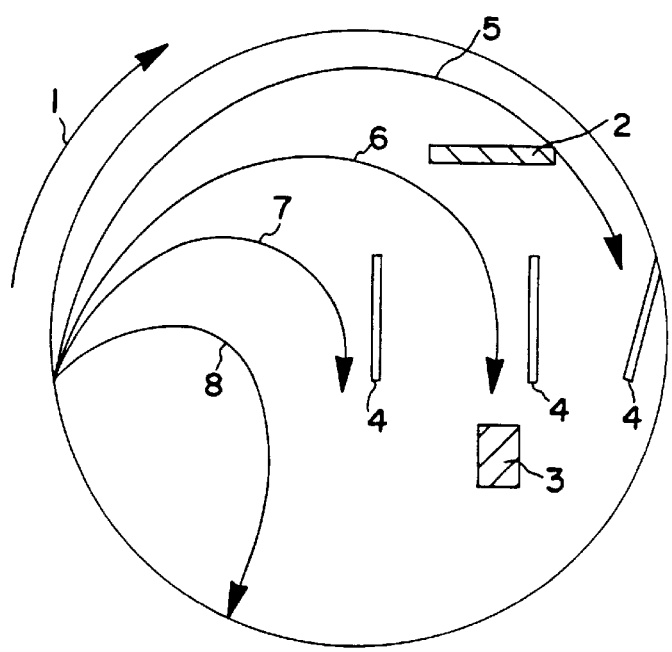
FIG. 4 shows diagrammatically one embodiment of the method to form granules.

FIG. 4 illustrates an additional process and apparatus for forming granules in a continuous operation. The coating operation occurs in a rotating pan set at an angle. Fresh powder is continuously added to the pan at the 12 to 3 o'clock position. As the pan rotates a stream of powder flows from top to bottom of the pan. The spray of nematode slurry is directed into this powder stream.

The spray device is designed to produce individual drops of nematode slurry, which are rapidly coated by powder to form granules. These soft granules compact and increase in density as they roll against each other in the bottom left portion of the pan. Fully formed and hardened granules discharge continuously from the pan and are directed by means of a chute into storage containers.

Additional equipment, routinely used to handle powders, is required to blend the individual dry ingredients and deliver a uniform flow of powder to the granulating pan.

The references cited above are all incorporated by reference herein, whether specifically incorporated or not.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features.

What is claimed is:

1. A composition for storage of viable infective juvenile nematodes comprising granules having a soft core consisting essentially of a purified preparation of viable infective juvenile nematodes of a family selected from the group consisting of Steinernematidae, Heterorhabditidae and Phasmarhabditidae supplied in an individual drop of liquid aqueous medium, wherein said core is coated with a powdered material wherein said aqueous medium within the drop is drawn into the powdered material, causing the powdered material to form a solidified casing surrounding said nematodes wherein more than 90% of the infective juvenile nematodes survive when maintained for six weeks at 25° C., or four weeks at 30° C., or use less than 1 ml $O_2$ per $10^6$ nematodes per day when stored at 25° C.

2. The composition of claim 1 wherein said powdered material consists essentially of at least one material selected from the group consisting of a silica, a clay, a diatomaceous earth, a hydroxyethyl cellulose, a lignosulfonate, a modified starch, and a superabsorbent.

3. The composition of claim 1 which further comprises at least one of an antibacterial agent, an antifungal agent, a surfactant, a viscosifier, a stabilizing agent and an ultraviolet light-absorbing agent.

4. A method for preparing a composition for storage of a purified preparation of viable infective juvenile nematodes of a family selected from the group consisting of Steinernematidae, Heterorhabditidae and Phasmarhabditidae, comprising contacting individual drops of a suspension of said infective juvenile nematodes in a liquid aqueous medium with a powdered material such that said powdered material completely surrounds each of said drops, wherein said aqueous medium within the drops is drawn into the powdered material causing the powdered material to form a solidified casing surrounding said nematodes, wherein more than 90% of the infective juvenile nematodes survive when maintained for six weeks at 25° C., or four weeks at 30° C., or use less than 1 ml $O_2$ per $10^6$ nematodes per day when stored at 25° C.

5. The method of claim 4 wherein contacting is performed by applying said drops to said powdered material.

6. The method of claim 4 wherein said powdered material is in motion at the time of said contacting.

7. The method of claim 6 wherein said motion is rotation or vibration.

8. The method of claim 4 wherein said contacting is performed by spraying droplets of said suspension into a falling curtain of powdered material.

9. The method of claim 4 wherein said contacting is performed by applying droplets to a powdered material suspended in an air-suspended fluidized bed or counter-current fluidized bed apparatus.

10. The method of claim 4 wherein said powdered material consists essentially of at least one material selected from the group consisting of a silica, a clay, a diatomaceous earth, a hydroxyethyl cellulose, a lignosulfonate, a modified starch, a surfactant, and a superabsorbent.

* * * * *